United States Patent [19]

Shah

[11] 4,116,201

[45] Sep. 26, 1978

[54] CATHETER WITH INFLATION CONTROL DEVICE

[75] Inventor: Nayan S. Shah, Carpentersville, Ill.

[73] Assignee: The Kendall Company, Boston, Mass.

[21] Appl. No.: 752,761

[22] Filed: Dec. 20, 1976

[51] Int. Cl.² .............................................. A61M 25/00
[52] U.S. Cl. .............................. 128/351; 128/349 BV; 137/226; 137/493; 137/512.5
[58] Field of Search ............ 128/348, 349 B, 349 BV, 128/350 R, 351, 274; 137/102, 226, 493, 512.3, 512.5, 508

[56] References Cited

U.S. PATENT DOCUMENTS

| 1,724,063 | 8/1929 | Anderson | 137/508 |
| 3,491,786 | 1/1970 | Crossman et al. | 137/226 X |
| 3,543,759 | 12/1970 | McWhorter | 128/349 BV |
| 3,633,586 | 1/1972 | Sheridan | 128/351 |
| 3,985,141 | 10/1976 | Stanley et al. | 128/351 |
| 4,044,793 | 8/1977 | Krueger et al. | 128/349 BV X |

Primary Examiner—Dalton L. Truluck
Attorney, Agent, or Firm—Powell L. Sprunger

[57] ABSTRACT

A catheter comprising, an elongated shaft, an inflatable balloon secured to the shaft, and an inflation lumen extending along the shaft and communicating with the balloon. The catheter has valve means communicating with the inflation lumen, with the valve means being normally closed and being openable to pump fluid into the inflation lumen for inflating the balloon. The catheter also has vent means communicating with the inflation lumen, with the vent means being normally closed and opening responsive to closure of the valve means and a pressure in the balloon above a predetermined amount, such that the vent means relieves pressure in the balloon above the predetermined amount after inflation of the balloon.

17 Claims, 8 Drawing Figures

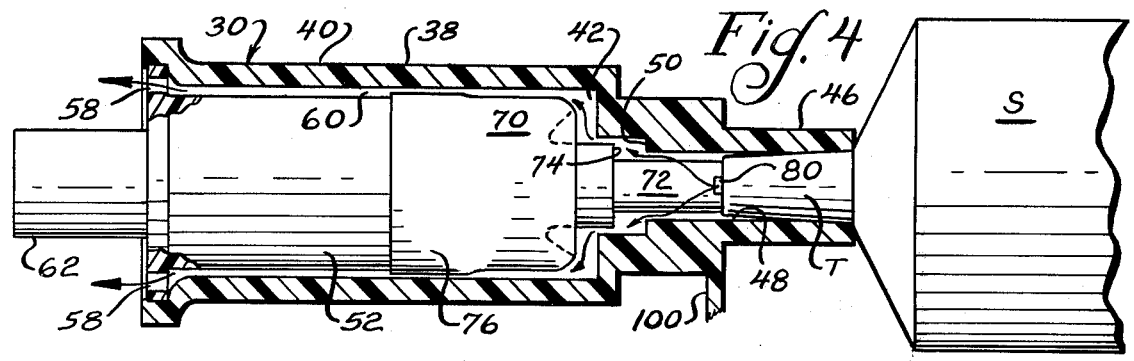
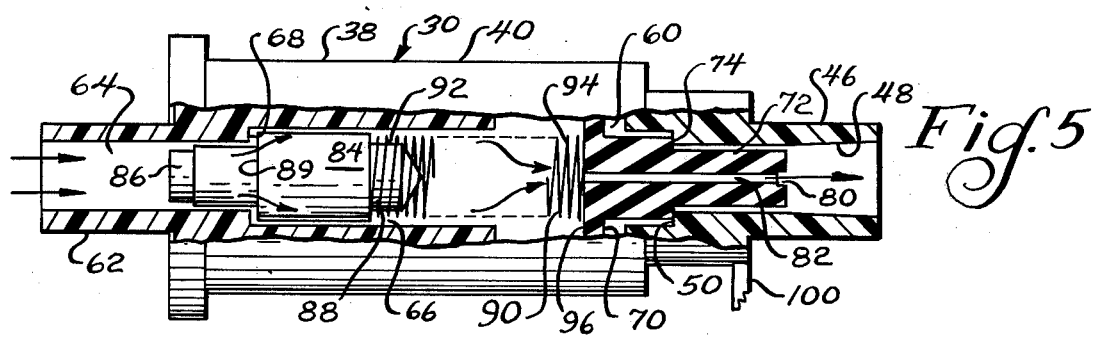
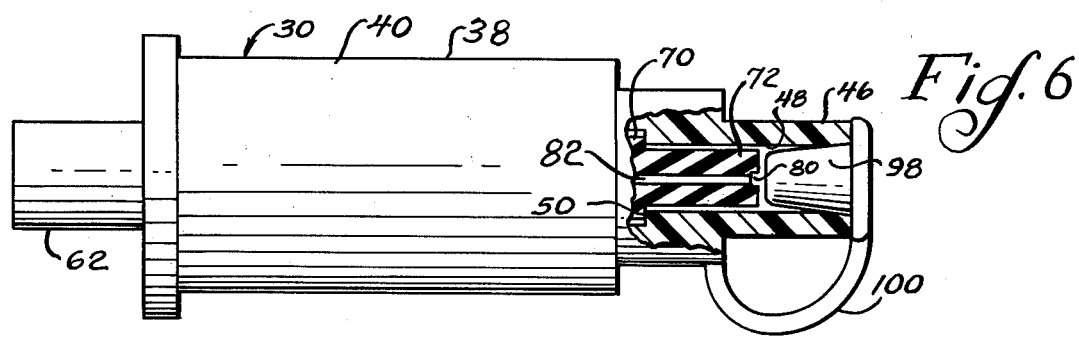
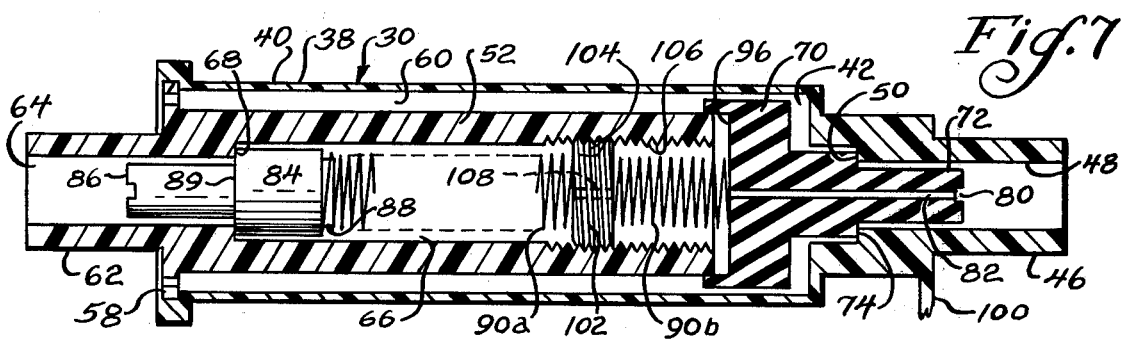
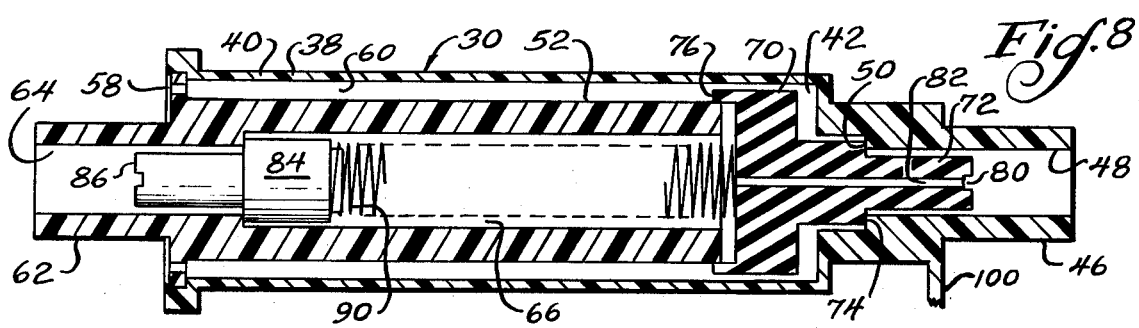

CATHETER WITH INFLATION CONTROL DEVICE

BACKGROUND OF THE INVENTION

The present invention relates to catheters, and more particularly to inflation control devices for such catheters.

A various assortment of catheters, such as endotracheal tubes and Foley catheters, have been proposed for use on patients. Such catheters are normally constructed with a shaft having a main lumen, an inflatable balloon secured to a distal end of the shaft, and an inflation lumen extending through a side arm of the catheter and along the shaft, with the inflation lumen communicating with the balloon. The catheters are normally provided with a valve on the side arm, which is located outside the patient during use of the catheter, in order to control inflation and deflation of the balloon. Although such catheters are in common use, a persistent problem with catheters has been determining an accurate inflation pressure in the balloon.

In the case of endotracheal tubes, the balloon or cuff if properly inflated seals off the trachea and retains the endotracheal tube in place. If the balloon has been inflated to a pressure less than the necessary amount, then the positive pressures developed by a respirator during use of the endotracheal tube may cause loss of seal by the cuff. On the other hand, if the cuff is overinflated, the contact of the cuff against the trachea frequently results in pressure necrosis of the tracheal mucosa. Thus, it is necessary that the cuff or balloon be inflated to a pressure sufficient to maintain a seal in the trachea, yet sufficiently small to minimize the possibility of necrosis. Of course, the inflated balloon is not directly visible to the physician, but even if visible, it is difficult to determine whether or not the balloon has been inflated to the desired pressure.

SUMMARY OF THE INVENTION

A principal feature of the present invention is the provision of an inflation control device for a catheter.

The catheter comprises, an elongated shaft, an inflatable balloon secured to the shaft, and an inflation lumen extending along the shaft and communicating with the balloon. The catheter has valve means communicating with the inflation lumen, with the valve means being normally closed and being openable to pump fluid into the inflation lumen for inflating the balloon. The catheter also has vent means communicating with the inflation lumen, with the vent means being normally closed and opening responsive to closure of the valve means and a pressure in the balloon above a predetermined amount.

A feature of the present invention is that the vent means relieves pressure in the balloon above the predetermined amount after inflation of the balloon.

Another feature of the invention is that the vent means opens responsive to closure of the valve means to prevent premature actuation of the vent means resulting from pressure transients during inflation of the balloon.

Still another feature of the invention is that the effective pressure at which the vent means opens is increased responsive to opening of the valve means.

Yet another feature of the invention is that the vent means is maintained closed during opening of the valve means and pumping of fluid through the inflation control device.

A feature of the invention is that the vent means closes during closure of the valve means and responsive to a pressure in the balloon less than the predetermined amount.

Thus, a feature of the present invention is that the valve means and vent means cooperate to establish the predetermined pressure in the inflation balloon.

Yet another feature of the invention is that the vent means may be selectively closed to permit further venting of the inflation balloon after the predetermined pressure has been established in the inflation balloon.

Thus, a feature of the present invention is that the inflation control device may be utilized to establish a relatively accurate pressure in the inflation balloon which is required to maintain a seal of the balloon against the traches and minimize the possibility of pressure necrosis.

Further features will become more fully apparent in the following description of the embodiments of this invention and from the appended claims.

DESCRIPTION OF THE DRAWINGS

In the drawings:

FIG. 4 is an elevational view, taken partly in section, illustrating the inflation control device during use for inflating a balloon or cuff on the endotracheal tube;

FIG. 5 is an elevational view, taken partly in section, illustrating the inflation control device during use for venting pressure from the balloon;

FIG. 6 is an elevational view, taken partly in section, showing the control device in a closed configuration during use of the endotracheal tube;

FIG. 7 is a sectional view of another embodiment of an inflation control device of the present invention; and FIG. 8 is a sectional view of another embodiment of an inflation control device of the present invention.

DESCRIPTION OF THE PREFERRED EMBODIMENTS

Figure 1:
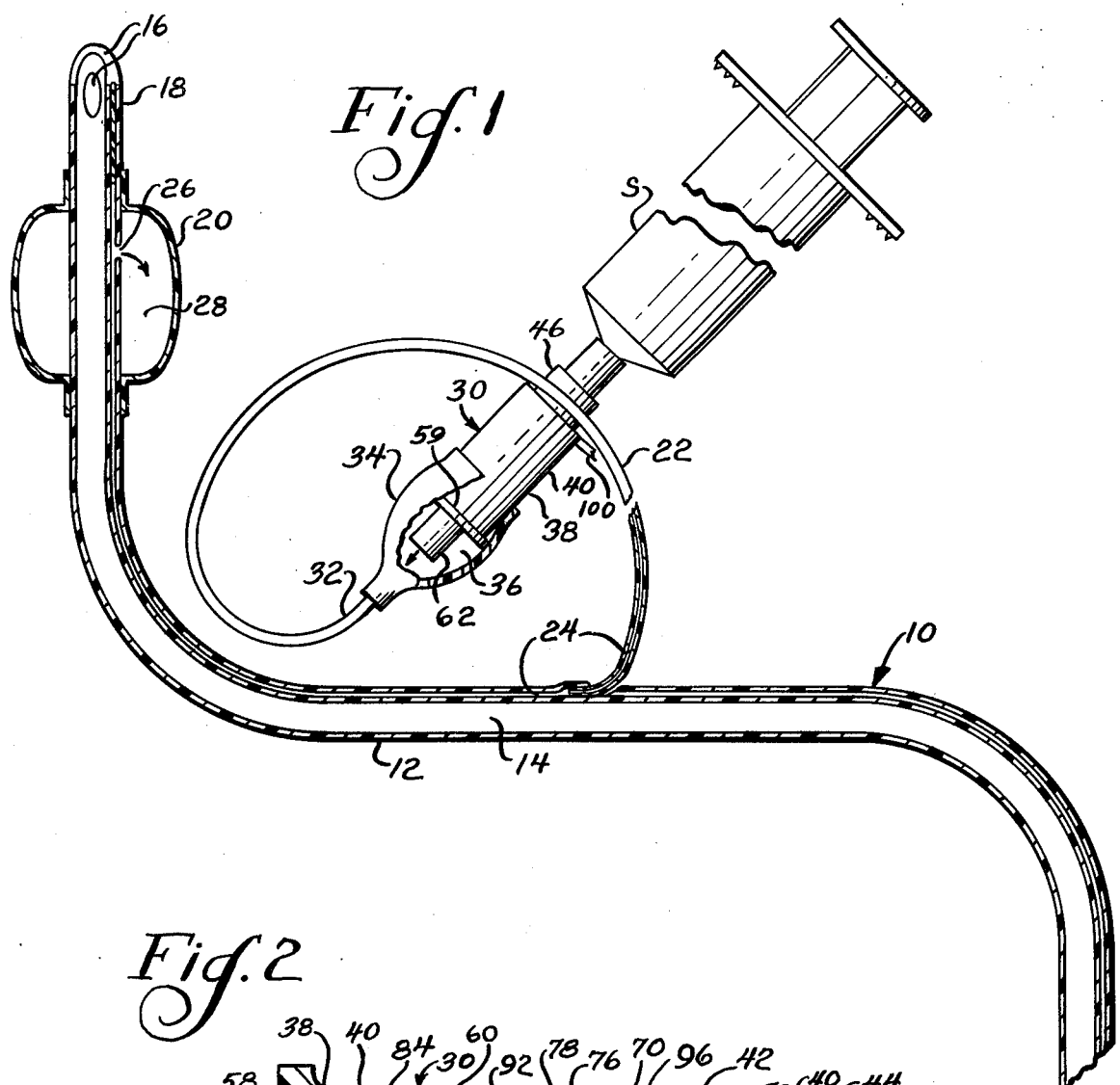
FIG. 1 is a fragmentary elevational view, taken partly in section and partly broken away, of an endotracheal tube having an inflation control device according to the present invention.

Referring now to FIG. 1, there is shown an endotracheal tube or catheter generally designated 10 having an elongated shaft or tube 12, a main lumen 14 extending through the shaft 12, openings 16 adjacent a distal end 18 of the shaft 12, and an inflatable balloon or cuff 20 secured to and surrounding the shaft 12 adjacent the distal end 18 of the shaft. The endotracheal tube 10 has a side arm 22, and an inflation lumen 24 extending through the side arm 22 and through a wall of the shaft 12, with the inflation lumen communicating through an opening 26 in the shaft 12 with a cavity 28 intermediate the balloon 20 and shaft 12. The endotracheal tube 10 also has an inflation control device generally designated 30 secured to an outer end 32 of the side arm 22 by any suitable means, such as a flexible sleeve 34 connected between the device 30 and the side arm 22 to establish communication between the device 30 and inflation lumen 24 through a cavity 36 in the sleeve 34. As will be further discussed below, a syringe S is utilized to pump fluid through the inflation control device 30, the inflation lumen 24 and into the cavity 28 in order to inflate the balloon 20, and the syringe S may be utilized to deflate the balloon 20 by withdrawing the fluid from the cavity 28 through the inflation lumen 24 and control device 30. Although, for convenience, the inflation control device 30 will be described primarily in connection with an endotracheal tube, it will be understood that the inflation control device may be utilized on any suitable catheter or similar device, such as a Foley catheter.

Figure 2:
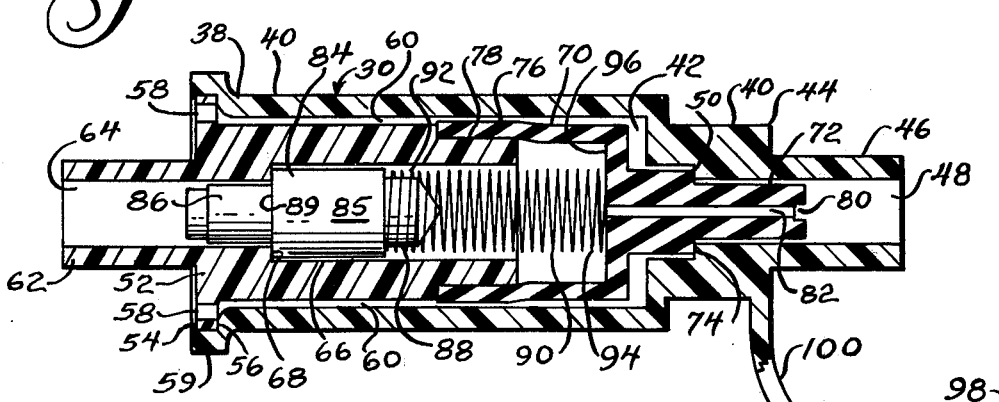
FIG. 2 is a sectional view of the inflation control device of FIG. 1.
Figure 3:
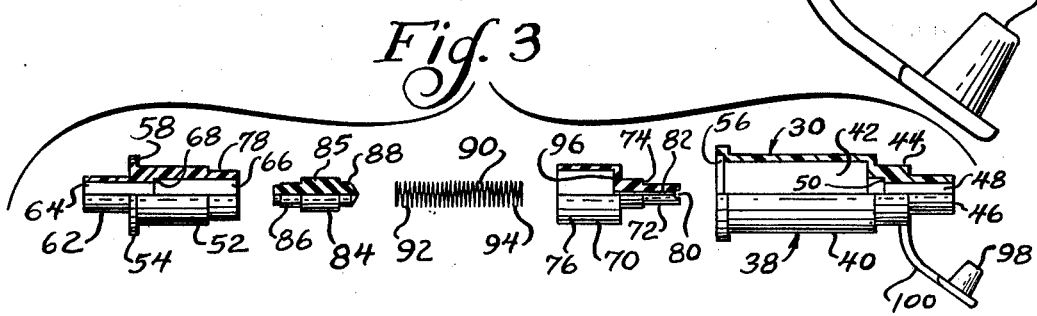
FIG. 3 is an exploded view, taken partly in section, of the inflation control device of FIG. 2.

With reference to FIGS. 2 and 3, the inflation control device or assembly 30 has a housing 38 having an outer cylindrical wall or casing 40 defining a first chamber 42. The outer wall 40 has an end portion 44 of reduced size adjacent an outer end 46 of the housing 38 defining a slightly tapered inflation port 48 to snugly receive a tip of the syringe, and an annular valve seat 50 adjacent an inner end of the inflation port 48. The housing 38 also has a generally cylindrical vent casing or inner wall 52 received in the first chamber 42 of the outer wall 40. As shown, the inner wall 52 has an annular flange 54 received in an annular recess 56 of the outer wall 40 adjacent an inner end 59 of the housing 38. The flange 54 has a plurality of openings 58 extending through the flange 54, and the flange 54 may be secured in the recess 56 by any suitable means, such as adhesive, in order to retain the inner wall 52 in place inside the outer wall 40. In this configuration, the inner wall 52 is spaced from the outer wall 40, such that the walls define an annular space or passageway means 60 intermediate the inner and outer walls and communicating with the flange openings 58. As shown, the inner wall 52 has a cylindrical extension 62 defining a vent lumen 64. Also, the inner wall 52 defines an inner second vent chamber 66, and an annular vent seat 68 intermediate the vent chamber 66 and vent lumen 64. With reference to FIG. 1, when the inflation control device 30 is secured to the side arm 22, the openings in the inner wall flange communicate with the inflation lumen 24, and the vent lumen in the extension 62 also communicates with the inflation lumen 24.

As shown in FIGS. 2 and 3, the inflation control device 30 has a flexible valve element 70 received in the first chamber 42. The valve element 70 has an elongated stem 72 received in the inflation port 48, an annular shoulder 74 adjacent an inner end of the stem 72 and sealingly engaging against the valve seat 50, and an annular sleeve 76 at an inner end of the valve element 70. As shown, the inner wall 52 has an annular groove 78 which receives an end portion of the sleeve 76 where it is retained in place. In this configuration, the sleeve 76 is spaced slightly from the outer wall 40 and defines an extension of the passageway means 60 between the inner wall 52 and the valve seat 50. Also, the valve element 70 defines an extension of the vent chamber 66, and separates the vent chamber 66 from the passageway means 60 in order to prevent passage of fluid therebetween. As shown, the valve element 70 has a lateral slot 80 at an outer end of the stem 72, and a channel 82 extending through the valve element 70 and communicating between the slot 80 and the vent chamber 66. The valve element may be made of any suitable material, such as rubber.

The inflation control device 30 also has a vent element 84 slidably received in the vent chamber 66. The vent element 84 may be made of any suitable material, and, in a preferred form, is made from a flexible material, such as rubber. The vent element 84 has an enlarged main body portion 85 received in the vent chamber 66, an inner stem 86 of reduced dimensions extending from an inner end of the main body portion 85 into the vent lumen 64, and an outer stem 88 extending from an outer end of the main body portion 85 in the vent chamber 66. The vent element 84 also has an annular shoulder 99 intermediate the inner stem 86 and the main body portion 85, with the shoulder 89 sealingly engaging against the vent seat 68.

In a preferred configuration, as shown, the vent element 84 is generally aligned with the valve element 70, and the device 30 has a helical spring 90 extending between the vent element 84 and valve element 70 in the vent chamber 66. An inner end 92 of the spring 90 is wound around the outer vent stem 88 and bears against the vent element 84 in order to bias the vent shoulder 89 in sealing engagement against the vent seat 68, while an outer end 94 of the spring 90 bears against an inner surface 96 of the valve element 70 in order to bias the valve shoulder 74 in sealing engagement against the valve seat 50. As will be further discussed below, the spring 90 permits movement of the valve element 70 and vent element 84 away from the respective seat in order to permit passage of fluid past the seat, and the spring 90 is selected such that the vent element actuates to permit passage of fluid through the vent means at a predetermined pressure in the inflatable balloon and vent lumen 64. In this regard, the dimensions of the inner stem 86 are slightly less than the dimensions of the vent lumen 64, and the main body portion 85 has dimensions slightly less than the inner surface of the vent chamber 66 in order to permit passage of fluid through the vent lumen 64 and vent chamber 66 around the vent element 84 when the vent means is actuated by a pressure above the predetermined amount.

The inflation control device also has a tapered plug 98 connected to the outer wall 40 by a strap 100 adjacent the outer end 46 of the housing 38. The plug 98 is of a size to be snugly received in the inflation port 48 and sealingly engage against an inner surface of the port 48, thus preventing passage of fluid from the device, as will be further described below. In the normal configuration of the device 30, the spring 90 urges the vent element 84 against the vent seat 68 and prevents passage of fluid through the venting means. Also, the spring 90 urges the valve element 70 against the valve seat 50 in order to prevent passage of fluid through the valve means. As previously discussed, the plug 98 is normally positioned in the inflation port 48 in order to prevent passage of fluid from the vent means through the inflation port 48. Thus, in the normal configuration, once inflated, the inflation control device 30 prevents escape of fluid from the balloon.

The use of the device 30 during inflation of the ballon is described in connection with FIG. 4. As shown, after the plug is removed from the inflation port 48, the tip T of the syringe S is inserted into the inflation port 48 resulting in sealing engagement of the tip with the inner surface of the port. The length of the valve stem 72 is selected relative the length of the syringe tip T, such that the syringe tip T contacts the outer end of the valve stem 72 and flexes the valve element 70 causing movement of the valve shoulder 74 away from the valve seat 50. Thus, in this configuration, the valve element 70 permits passage of fluid, such as air or water, between the valve shoulder 74 and valve seat 50. In addition, with reference to FIG. 2, the flexed valve element 70 causes compression of the spring 90, and biases the vent element 84 with a greater force against the vent seat 68 in order to increase the effective pressure at which the vent means actuates. Referring again to FIG. 4, as indicated by the direction of the arrows in the drawing, fluid is ejected through the spyringe tip T into the slot 80 of the valve element 70, after which it passes from the ends of the slot 80 around the side of the valve stem 72, between the valve shoulder 74 and valve seat 50, through the passageway means 60 and openings 58 into the cavity 36 of the sleeve 34 previously described in connection with FIG. 1. The fluid then passes through the inflation lumen 24 of the side arm 22 and shaft 12 into the balloon causing inflation of the balloon 20. Thus, the syringe is attached to the inflation control device in order to open the valve means, and the fluid is pumped from the syringe through the valve means of the device 30 to inflate the balloon. At the same time, with reference to FIG. 2, it will be apparent that fluid passes from the slot 80 of the valve element 70 through the channel 82 into the vent chamber 66 in order to increase the pressure in the vent chamber 66 and prevent movement of the vent element 84 away from the vent seat 68. In this manner, the vent means is prevented from actuating and remains closed during inflation of the balloon. According to a preferred inflation procedure, as will be further discussed below, the balloon is slightly overinflated in order to obtain an accurate final pressure desired in the inflated balloon.

After the inflation procedure has been completed, the syringe tip is removed from the inflation port 48, as shown in FIG. 5. As a result, the spring 90 biases the valve shoulder 74 against the valve seat 50 in sealing engagement to close the valve means and prevent passage of fluid from the passageway means 60 into the inflation port 48. At the same time, the pressure previously generated by the syringe in the vent chamber 66 is no longer present and tension previously caused by the flexed valve element 70 is released from the spring 90 such that the spring 90 may accurately control actuation of the vent element 84 of the venting means. Thus, if the balloon has been inflated to a pressure above the predetermined amount, the excessive balloon pressure causes movement of the vent element 84 away from the vent seat 68 as controlled by the spring 90. In this configuration, with reference to FIGS. 1 and 5, the inflation fluid passes from the balloon 20 through the inflation lumen 24, the vent lumen 64, around the vent element 84 between the vent shoulder 89 and vent seat 68, and into the vent chamber 66, after which it passes from the vent chamber 66 through the channel 82 of the valve element 70 and outside of the housing 38. In this manner, pressure is relieved from the overinflated balloon through the venting means.

When a sufficient amount of fluid has escaped through the inflation control device 30 and the predetermined desired pressure has been attained in the balloon 20, the spring 90 urges the vent element 84 against the vent seat 68 in sealing engagement in order to prevent further passage of fluid between the vent shoulder 89 and vent seat 68. Thus, when the vent means closes, the desired pressure has been obtained in the balloon. At this time, with reference to FIG. 6, the plug 98 is inserted into the inflation port 48 in order to close the port 48 and prevent passage of fluid out of the device 30. Accordingly, the plug 98 prevents effective actuation of the vent means which otherwise might be caused during use of the endotracheal tube due to a positive pressure generated by a respirator or possibly by patient breathing. Of course, if the pressure in the balloon is less than the predetermined amount after inflation of the balloon has been completed, the vent means will not be actuated and remains closed prior to placement of the plug 98 in the inflation port 48. However, as previously indicated, it is preferable to slightly overinflate the balloon during the inflation procedure in order that the vent means actuates and results in an accurate final pressure in the balloon as controlled by the vent means after the valve means has closed. In this manner, a desired pressure may be obtained in the balloon which is sufficiently large to prevent loss of seal by the cuff in the patient's trachea during use of the endotracheal tube, yet is sufficiently small to minimize the possibility of pressure necrosis to the patient.

After use of the endotracheal tube has been completed, the syringe tip is again inserted into the inflation port of the device 30, such that the syringe tip flexes the valve element 70, in a manner as previously described in connection with FIG. 4. Next, the syringe may be utilized to withdraw the fluid from the balloon, with the fluid passing through the inflation lumen and passageway means 60 into the syringe. After removal of the syringe tip from the port 48, the valve element 70 again assumes its sealing configuration against the valve seat 50.

Thus, in accordance with the present invention, the balloon or cuff may be readily inflated by attaching the syringe to the inflation control device, after which the inflation fluid is ejected from the syringe through the device and into the balloon. At the same time, the opened valve means and the pressure generated by the syringe during balloon inflation prevents opening of the vent means. After the inflation procedure has been completed, the syringe is removed from the inflation control device, and the vent means actuates responsive to closure of the valve means and a pressure in the balloon greater than the predetermined pressure in order to relieve pressure from the balloon and achieve a final accurate pressure in the balloon. After the desired pressure has been obtained in the balloon, the vent means closes to prevent further escape of fluid from the balloon, and the inflation control device is closed in order to maintain the desired final pressure in the balloon during use of the catheter. Thus, the valve means and vent means cooperate with each other in order to prevent premature actuation of the vent means and to achieve an accurate predetermined pressure in the balloon.

Another embodiment of the present invention is illustrated in FIG. 7, in which like reference numerals designate like parts. In this embodiment, the device 30 has a plate 102 extending across the vent chamber 66. In the particular embodiment shown, the plate 102 may have outer threads 104 received in threads 106 on the inner surface of the inner wall 52, thus permitting selective adjustment of the plate position longitudinally in the vent chamber 66. Also, the plate 102 has an aperture 108 extending through the plate 102 to permit passage of fluid through the plate in the chamber 66. As shown, the device 30 has a first helical spring 90a extending between one side of the plate 102 and the vent element 84. The device 30 also has a second helical spring 90b extending between the other surface of the plate 102 and the inner surface 96 of the valve element 70. In a preferred form, the second spring 90b is relatively heavy and strong, such that it causes rapid closure of the valve element 70 against the valve seat 50, and the first spring 90a is separately selected to provide accurate closure of the vent element 84 against the vent seat 68. Thus, in this embodiment of the invention, the device has separate springs for applying different forces against the valve and vent elements to provide separate control of the elements during opening and closure. In other respects, the device 30 of FIG. 7 operates in a manner similar to that described in connection with FIGS. 1-6, with the exception that the valve element is slidably received on the inner wall 52, as will be described below in connection with FIG. 8.

Thus, another embodiment of the present invention is illustrated in FIG. 8, in which like reference numerals designate like parts. In this embodiment, the valve element 70 may be made of a relatively rigid material, and the inner sleeve 76 of the valve element 70 is slidably received on the outer surface of the inner wall 52. As before, when the syringe tip is inserted into the device 30, the tip contacts the valve stem 72 and moves the valve element to a retracted position with the valve shoulder 74 spaced from the valve seat 50 while the valve sleeve 76 slides on the outer surface of the inner wall 52. If desired, an O-ring may be placed between the outer surface of the inner wall 52 and the valve sleeve 76 and between the valve shoulder 74 and valve seat 50 for improved sealing characteristics. In other respects, the device of FIG. 8 is similar to the device previously described in connection with FIGS. 1-6.

The foregoing detailed description is given for clearness of understanding only, and no unnecessary limitations should be understood therefrom, as modifications will be obvious to those skilled in the art.

I claim:

1. A catheter, comprising:
an elongated shaft;
an inflatable balloon secured to the shaft;
an inflation lumen extending along the shaft and communicating with the balloon;
valve means communicating with the inflation lumen, said valve means being normally closed and being openable to pump fluid into the inflation lumen for inflating said balloon; and
vent means communicating with the inflation lumen, said vent means being normally closed and only opening in response to closure of the valve means and a pressure in the balloon above a predetermined amount, said vent means relieving pressure in the balloon above said predetermined amount after inflation of the balloon; and
means for increasing the effective pressure at which the vent means opens responsive to opening of the valve means and preventing actuation of the vent means while the valve means is open.

2. The catheter of claim 1 wherein the catheter comprises an endotracheal tube.

3. The catheter of claim 1 including means for selectively closing said vent means.

4. The catheter of claim 1 including means for closing the vent means responsive to closure of the valve means and a pressure in the balloon less than said predetermined amount.

5. The catheter of claim 1 including means for closing the vent means responsive to opening of the valve means and pumping of fluid through the valve means.

6. A catheter, comprising:
an elongated shaft;
an inflatable balloon secured to the shaft;
an inflation lumen extending along the shaft and communicating with the balloon; and
an inflation control assembly comprising,
a housing having a valve seat and passageway means communicating between the valve seat and the inflation lumen,
a valve element received in the housing and having channel means extending through the valve element,
means for biasing the valve element against the valve seat to normally prevent passage of fluid between the passageway means and the outside of the housing, said valve element being movable from the valve seat to permit passage of fluid into the passageway means for inflating the balloon, and
vent means communicating between the inflation lumen and said channel means, said vent means being normally closed and opening responsive to pressure in the balloon above a predetermined amount to permit passage of fluid from the inflation lumen through said channel means.

7. A catheter, comprising:
an elongated shaft;
an inflatable balloon secured to the shaft;
an inflation lumen extending along the shaft and communicating with the balloon; and
an inflation control assembly comprising,
a housing having an inflation port, passageway means communicating with the inflation lumen, a valve seat intermediate the passageway means and said port, and an inner chamber having a vent seat intermediate the chamber and inflation lumen,
a valve element received in the housing and closing an end of said chamber remote the vent seat from the passageway means, said valve element having channel means communicating between the chamber and the atmosphere exterior said valve seat,
means for biasing the valve element against the valve seat to normally prevent passage of fluid between the passageway means and said port, said valve element being movable away from the valve seat to permit passage of fluid through the passageway means for inflating the balloon,
a vent element received in said chamber, and
means for biasing said vent element against the vent seat to normally prevent passage of fluid between the inflation lumen and chamber, said vent element being movable away from the vent seat responsive to a pressure in the balloon above a predetermined amount to permit passage of fluid from the inflation lumen past the vent seat and through the chamber and channel means to the outside of the housing.

8. The catheter of claim 7 including a cap for selectively closing the inflation port and channel means.

9. The catheter of claim 7 wherein the biasing means comprises, means for commonly urging the valve element against the valve seat and the vent element against the vent seat.

10. The catheter of claim 9 wherein the urging means comprises a helical spring extending between adjacent ends of the valve and vent elements.

11. The device of claim 7 wherein the biasing means comprises, means for separately urging the valve element against the valve seat and the vent element against the vent seat.

12. The catheter of claim 11 wherein the urging means biases the vent element against the vent seat with a first force to permit accurate response of the vent element responsive to pressure in the balloon, and separately biases the valve element against the valve seat with a relatively large second force to provide rapid closure of the valve element against the valve seat.

13. The catheter of claim 11 wherein the urging means comprises, a plate extending across the chamber and having opening means to permit passage of fluid through the plate, a first helical spring extending between the plate and the vent element, and a second helical spring extending between the plate and the valve element.

14. The catheter of claim 7 wherein the valve element comprises a flexible plug.

15. The catheter of claim 7 wherein the valve element comprises a rigid plug slidably received in the housing.

16. A catheter, comprising:
an elongated shaft;
an inflatable balloon secured to the shaft;
an inflation lumen extending along the shaft and communicating with the balloon; and
an inflation control assembly comprising,
a housing having an outer wall defining a first chamber, an inflation port adjacent an outer end of the housing, and a valve seat adjacent the port, said housing having an inner wall positioned in the first chamber and defining an inner second chamber, passageway means intermediate the inner and outer walls communicating with the inflation lumen, a vent lumen adjacent an inner end of the housing communicating with the inflation lumen, and a vent seat intermediate the vent lumen and second chamber, said inner wall being open at the outer end thereof,
a valve element received in the first chamber on the outer end of the inner wall, said valve element defining an extension of the passageway means between the inner wall and valve seat and closing the second chamber from the passageway means, said valve element having a stem extending into the inflation port with the stem having a lateral central slot at its outer end, a channel extending between the slot and an inner end of the valve element and communicating with the second chamber, and a shoulder for sealingly engaging against the valve seat,
means for biasing the valve element against the valve seat to normally prevent passage of fluid between the passageway means and inflation port, said valve element being movable from the valve seat to permit passage of fluid into the passageway means and inflation lumen for inflating the balloon,
a vent element received in the second chamber and having a shoulder for sealingly engaging against the vent seat, and
means for biasing the vent element against the vent seat to normally prevent passage of fluid between the vent lumen and second chamber, said vent element being movable away from the vent seat responsive to a pressure in the balloon above a predetermined amount.

17. The catheter of claim 16 wherein the housing includes flange means connecting the inner and outer walls adjacent an inner end of the housing, said flange means having aperture means communicating between the passageway means and the inflation lumen.

* * * * *